US006238659B1

(12) United States Patent
Rösl et al.

(10) Patent No.: US 6,238,659 B1
(45) Date of Patent: May 29, 2001

(54) AGENT FOR TREATING PAPILLOMA VIRUS-POSITIVE MALIGNANT AND PREMALIGNANT LESIONS

(75) Inventors: Frank Rösl, Neuhofen; Harald Zur Hausen, Hirschberg, both of (DE)

(73) Assignee: Deutsches Krebsforschungszentrum Stiftung Des Öffentlichen Rechts, Heidelberg (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/817,677

(22) PCT Filed: Oct. 5, 1995

(86) PCT No.: PCT/DE95/01395

§ 371 Date: Sep. 4, 1997

§ 102(e) Date: Sep. 4, 1997

(87) PCT Pub. No.: WO96/11004

PCT Pub. Date: Apr. 18, 1996

(30) Foreign Application Priority Data

Oct. 5, 1994 (DE) .................................. 44 35 661

(51) Int. Cl.$^7$ ...................................... A61K 38/19
(52) U.S. Cl. .............................. 424/85.1; 514/2; 514/12; 514/71; 514/198
(58) Field of Search .................... 514/71, 198, 2, 514/12; 424/85.1

(56) References Cited

U.S. PATENT DOCUMENTS 5,686,436 * 11/1997 Van Dyke ......................... 514/171

FOREIGN PATENT DOCUMENTS 2113683 7/1995 (CA) .
0 527 241 A1 2/1993 (EP) .

OTHER PUBLICATIONS

Rösl et al., 1994, "Differential Regulation of the JE Gene Encoding the Monocyte Chemoattractant Protein (MCP–1) in Cervical Carcinoma Cells and Derived Hybrids," *J. Virol.* 68(4):2142–2150.

* cited by examiner

Primary Examiner—Elizabeth Kemmerer
(74) Attorney, Agent, or Firm—Pennie & Edmonds LLP

(57) ABSTRACT

The present invention relates to a preparation comprising a substance influencing the cellular redox state for treating papilloma virus-positive malignant lesions.

5 Claims, No Drawings

AGENT FOR TREATING PAPILLOMA VIRUS-POSITIVE MALIGNANT AND PREMALIGNANT LESIONS

This is a national phase filing of the Application No. PCT/DE95/01395, which was filed with the Patent Corporation Treaty on Oct. 5, 1995, and is entitled to priority of the German Patent Application P 44 35 661.7 filed Oct. 5, 1994.

I. FIELD OF THE INVENTION

The present invention relates to the use of a preparation comprising a substance influencing the cellular redox state for treating papilloma virus-positive malignant and premalignant lesions.

II. BACKGROUND OF THE INVENTION

It is well known to treat lesions which are caused by human-pathogenic papilloma viruses (HPV) by the application of cytokines, such as α-tumor necrosis factor and interferons. For this purpose, cytokines are administered in high doses. The treatment of patients exposed to high cytokine doses is accompanied by considerable side-effects such as cachexia, queasiness, vomiting and headache.

Therefore, it is the object of the present invention to provide a preparation for treating papilloma virus-positive malignant and premalignant lesions, by which the above side-effects are reduced.

According to the invention this is achieved by using a preparation comprising a substance influencing the cellular redox state.

III. SUMMARY OF THE INVENTION

The present invention relates to a preparation comprising a substance influencing the cellular redox state for treating papilloma virus-positive malignant lesions.

IV. DETAILED DESCRIPTION OF THE INVENTION

The expression "a substance influencing the cellular redox state" comprises compounds of any kind which can reduce the redox state of cells, particularly of host cells of papilloma viruses. They may be, e.g., exogenous compounds. Examples of the above compounds are antioxidants such as pyrrolidine-dithiocarbamate (PDTC) and derivatives thereof. The compounds included in the preparation used according to the invention may also be metabolized into the actual substance influencing the cellular redox state as late as in the cell to be treated.

The preparations used according to the invention may also contain several of the substances.

In order for the modulator substance to display its effect, it has to be both intracellularly and extracellularly sufficiently stable within the body, i.e., it may not be metabolized to give an ineffective compound before it has displayed its effect. A person skilled in the art knows which factors influence the stability. Moreover, he knows for how long a compound has to be stable to display its effect. In addition, he is familiar with tests of how to determine the stability of the compounds.

In a preferred embodiment, the preparation also includes a cytokine. Examples thereof are interferons and α-tumor necrosis factor (TNF-α). Recombinant interferon and recombinant α-TNF are used preferably. The cytokine dose administered with the preparations used according to the invention is lower than the cytokine dose administered so far. Thus, the positive effect of cytokines can be achieved by the preparation used according to the invention without resulting in the above drawbacks thereof. The effect of the substance influencing the cellular redox state is also increased when a cytokine is present.

Conjugates according to the invention distinguish themselves in that they have little side-effects. Thus, they are suited in the best possible way for the treatment of papilloma virus-positive, particularly HPV-positive, malignant and premalignant lesions such as carcinomas of the genital zone. This also includes warts.

The below examples explain the invention in more detail. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description. Such modifications are intended to fall within the scope of the appended claims.

V. EXAMPLES

A. Example 1

Reduction of HPV 18 Transcription by PDTC

HPV-positive cells (DEM medium 10% fetal calf serum (BRL), 1% penicillin/streptomycin) are incubated with PDTC (from Sigma, dissolved in serum-free DEM medium directly before the start of the experiment; final concentration: 100 $\mu$M) under conventional conditions. About 70% reduction of the HPV 18 transcription occurs after 6 hours (assay technique: conventional "Northern" blot analysis). The reduction of the HPV 18 transcription is an indicator of the reduced cell growth of the HPV-positive cells and thus also of the therapeutic effectiveness.

B. Example 2

Suppression of the HPV 18 (Specific RNA) Transcription by a Combination of PDTC and TNF-α

Non-tumorous cell hybrids between HPV 18-positive cervical carcinoma cells (HeLa) and human fibroblasts are incubated with 100 to 150 units/ml TNF-α and 100 $\mu$M PDTC. The RNA is extracted after 12 to 14 hours. An almost complete suppression of the HPV 18 transcription results under these conditions.

If TNF-α is used alone, the same suppression effect can be observed with about 500 units/ml TNF-α.

As follows from the above results, the TNF-α dose can be reduced as compared the sole administration of TNF-α by simultaneous administration of PDTC and TNF-α, with the same effect being obtained.

All references cited within the body of the instant specification are hereby incorporated by reference in their entirety.

What is claimed:

1. A method for treating a papilloma virus-positive lesion, comprising administering a pharmaceutical composition comprising a compound influencing the cellular redox state, a cytokine, and conventional auxiliary agents to a subject in need, wherein the compound influencing the cellular redox state is a pyrrolidine dithiocarbamate or a derivative thereof.

2. The method of claim 1, wherein the cytokine is α-tumor necrosis factor.

3. The method of claim 1, wherein said papilloma virus-positive lesion is a benignant lesion.

4. The method of claim 1, wherein said papilloma virus-positive lesion is a pre-malignant lesion.

5. The method of claim 1, wherein said papilloma virus-positive lesion is a malignant lesion.

* * * * *